US006558706B2

(12) United States Patent
Kantor et al.

(10) Patent No.: US 6,558,706 B2
(45) Date of Patent: May 6, 2003

(54) MICROENCAPSULATED FRAGRANCES AND METHOD FOR PREPARATION

(75) Inventors: Martin L. Kantor, Mamaroneck, NY (US); Evgueni Barantsevitch, Scarsdale, NY (US); Sam J. Milstein, Larchmont, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 10/062,829

(22) Filed: Jan. 31, 2002

(65) Prior Publication Data

US 2002/0102286 A1 Aug. 1, 2002

Related U.S. Application Data

(63) Continuation of application No. 08/873,780, filed on Jun. 12, 1997.
(60) Provisional application No. 60/019,913, filed on Jun. 14, 1996.

(51) Int. Cl.[7] .............................. A61K 9/14; A61K 9/00; A61K 9/04
(52) U.S. Cl. .................. 424/489; 424/76.1; 424/76.4; 424/486
(58) Field of Search .................. 424/489, 49, 76.1, 424/76.4, 486

(56) References Cited

U.S. PATENT DOCUMENTS

| 4,136,250 A | 1/1979 | Mueller et al. ............... 528/29 |
| 4,181,708 A | 1/1980 | Dannelly ....................... 424/19 |
| 4,181,710 A | 1/1980 | Dannelly et al. .............. 424/33 |
| 4,196,187 A | 4/1980 | Dannelly et al. .............. 424/21 |
| 4,464,271 A | 8/1984 | Munteanu et al. ............ 252/8.6 |
| 4,568,560 A * | 2/1986 | Schobel ......................... 424/49 |
| 4,780,315 A | 10/1988 | Wu et al. ..................... 424/438 |
| 4,842,761 A | 6/1989 | Rutherford .................... 252/90 |
| 5,008,115 A | 4/1991 | Lee et al. ..................... 424/486 |
| 5,246,603 A | 9/1993 | Tsaur et al. .................... 525/86 |
| 5,281,357 A | 1/1994 | Morgan et al. ............. 252/174 |
| 5,385,959 A | 1/1995 | Tsaur et al. .................... 524/17 |
| 5,492,646 A | 2/1996 | Langley et al. ............. 252/174 |
| 5,508,024 A | 4/1996 | Tranner et al. ................ 424/59 |
| 5,576,286 A | 11/1996 | Karp et al. ..................... 512/2 |
| 5,824,345 A | 10/1998 | Milstein ....................... 424/489 |
| 6,024,943 A | 2/2000 | Ness et al. ..................... 424/59 |
| 6,375,983 B1 | 4/2002 | Kantor et al. ................ 424/489 |

FOREIGN PATENT DOCUMENTS

| EP | 0067533 | 12/1982 | ............ B01J/13/02 |
| WO | 9421234 | 9/1994 | .......... A61K/9/107 |
| WO | 9747288 | 12/1997 | ............ A61K/9/48 |

* cited by examiner

Primary Examiner—Thurman K. Page
Assistant Examiner—Blessing Fubara
(74) Attorney, Agent, or Firm—Darby & Darby

(57) ABSTRACT

This invention provides an encapsulated fragrance in which the fragrance is controlled can be released by exposing the encapsulated fragrance to a solution of a predetermined pH. The invention also contemplates a process for preparing encapsulated fragrances.

12 Claims, No Drawings

MICROENCAPSULATED FRAGRANCES AND METHOD FOR PREPARATION

This application claims priority pursuant to 35 U.S.C. §120 from U.S. Ser. No. 08/873,780, filed Jun. 12, 1997, which claims priority pursuant to 35 U.S.C. §119 from U.S. Provisional Application Serial No. 60/019,913 filed Jun. 14, 1996.

This invention relates to an encapsulated fragrance in which the fragrance is controlled can be released by exposing the encapsulated fragrance to a solution of a predetermined pH. The invention also contemplates a process for preparing encapsulated fragrances.

BACKGROUND OF THE INVENTION

There are numerous uses for a system which can release a fragrance in a controlled manner. These include the use of fragrances in substrates such as air fresheners, laundry detergents, fabric softeners, deodorants, lotions, and other household items. However, the design of a system that will release a fragrance over a period of time under repeatable predetermined conditions, has proved difficult. One problem in achieving such a design is that fragrances are generally essential oils that are composed of a plurality of compounds, each present in different quantities. Thus, it is difficult to predict how the quantity of each component of the essential oil will effect the release characteristics of the system.

U.S. Pat. No. 4,587,129 describes a method for preparing gel articles which contain up to 90% by weight of fragrance or perfume oils. The gels are prepared from a polymer having a hydroxy (lower alkoxy) 2-alkeneoate, a hydroxy (lower alkoxy) lower alkyl 2-alkeneoate, or a hydroxy poly (lower alkoxy) lower alkyl 2-alkeneoate and a polyethylenically unsaturated crosslinking agent. These materials are said to have continuous slow release properties, i.e., they release the fragrance component continuously over a long period of time. However, a drawback of the invention is that the release of the fragrance from the gels is continuous and cannot be controlled. Thus, the fragrance can be exhausted while the product in which it is contained is on the shelf, e.g., in storage, prior to use by the consumer.

A composition that functions to hold a fragrance until it is desirable to release the fragrance and then functions to release the fragrance over an extended period of time would be desirable. Thus, an object of this invention is to provide a composition which retains a fragrance until the desired time for release.

SUMMARY OF THE INVENTION

The subject invention provides compositions comprising a polymer and a fragrance, wherein said polymer comprises an acrylic acid copolymer. The acrylic acid copolymer comprises an acrylic acid monomer having the formula:

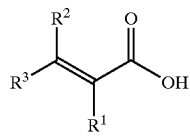

wherein $R^1$, $R^2$, and $R^3$ are independently selected from the group consisting of hydrogen and lower alkyl; and at least one ethylenically unsaturated polymerizable monomer such as acrylates, methacrylates, vinyl pyridines, vinyl ethers, acrylamides, methacrylamides, styrenes, pyrrolidones, and the like.

The fragrances useful in practicing the invention include any material which can impart a desirable odor or enhance an existing smell or odor to a substrate such as, for example air fresheners, laundry detergents, fabric softeners, deodorants, lotions, and other household items. Such fragrances generally contain at least one essential oil.

The compositions of the invention can controllably release a fragrance over an extended time period by contacting the composition with a solution having a pH which dissolves the polymer and releases the fragrance. In another embodiment, the polymer compositions of the invention may be used to form microspheres containing the fragrance.

Also contemplated is a method for preparing these compositions which comprises mixing the monomers and a fragrance and polymerizing the mixture.

DETAILED DESCRIPTION OF THE INVENTION

The present invention provides compositions which are useful for controlled release of fragrances. The compositions of the invention can encapsulate a fragrance and controllably release the fragrance upon exposure to a solution having a predetermined pH. The compositions of the invention comprise a polymer and a fragrance. The polymers useful in practicing the invention can encapsulate the fragrance and release it at the desired time. Any fragrance which can be solubilized in the organic phase of a polymerization emulsion, and which can add a smell or odor to a substrate or is desirable to change, improve or enhance an existing smell or odor of a substrate may be incorporated in the polymers.

The polymers useful in practicing the present invention comprise (a) an acrylic acid monomer and
(b) a second monomer having at least one polymerizable ethylenically unsaturated group, such as, for example, acrylates, methacrylates, vinyl pyridines, vinyl ethers, acrylamides, methacrylamides, pyrrolidones, styrenes, methacrylates, and the like.

The acrylic acid monomer has the formula:

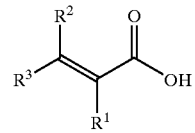

wherein $R^1$, $R^2$, and $R^3$ are independently selected from the group consisting of hydrogen and lower alkyl. These polymers can be used to encapsulate the fragrance until it is desired to release it.

The lower alkyl groups include groups having from 1 to about 6 carbon atoms. Preferred groups are methyl, ethyl, isopropyl and butyl.

Typically, fragrances or perfume agents are compounds or compositions that either increase or enhance an existing smell or odor, or that impart a specific agreeable smell or odor to a substrate. These fragrances may be solids, liquids, vapors, or any combination thereof. Furthermore, they may completely or partially change state before being incorporated into a microsphere, while incorporated in a microsphere, or after being partially or completely released from a microsphere. Non-limiting examples of fragrances include essential oils, such as, for example, d-limonene, eugenol, orange, lemon, eucalyptol (cineol), clove oil and the like. Also useful in practicing the invention are commercially available fragrances which include materials, such as, for example, Autre Melange, or MixTex 1 from Givaudan-Roure, France and the like.

The amount of acrylic acid monomer in the polymer can vary from about 20% to about 80% by weight. The preferred amount of acrylic acid is from about 40% to about 60% by weight.

The release of the fragrance can be controlled by the incorporation of a pH sensitive group in the polymer composition. Examples of pH sensitive groups include carboxyl and amine groups. It is then possible to protonate the amine groups or deprotonate the carboxyl groups to dissolve the polymers and release the fragrance.

The polymers of the invention are prepared by suspension polymerization. The monomers are emulsified with water and the resulting microglobules are polymerized in situ to solid microspheres. If an organic compound, such as most perfumes and fragrances, is added to the unpolymerized mixture, it will partition into the globules. During the polymerization, the fragrance compound becomes incorporated into the polymer or polymer microspheres and protected from volatilization.

These monomers are easy to polymerize and have a strong affinity for the perfume and fragrance materials. The polymerization can be initiated by methods that are well known to those skilled in the art, such as, for example, free-radical initiators, ultraviolet light; heat and the like. Non-limiting examples of free-radical initiators include 2-2', azobisisobutyronitrile (AIBN), benzoyl peroxide, cumene hydroperoxide, and the like. Suspending agents such as polyvinyl alcohol or polyvinylpyrrolidone may also be added to prevent the globules from agglomerating. If a water-soluble monomer is employed, neutral salts such as chlorides and sulfates can be added to cause phase separation.

The suspension polymerization reaction is stirred using standard equipment. The stirring rate is usually from about 200 RPM to about 800 RPM. The preferred rate is from about 250 RPM to about 400 RPM.

Polymerization can be carried out using standard additives known in the art. Examples of additives include stabilizers to reduce agglomeration; salts to reduce phase separation.

Non-limiting examples of stabilizers (suspending agents) include but are not limited to polyvinyl alcohol (PVA), polyvinyl pyrrolidone (PVP), polyacrylic acid (PAA), starch, gelatin, hydroxypropylmethyl cellulose phthalate (HPMCP) and the like. The stabilizing additives can be added in a range of from about 0.1 to about 5 percent and preferably at about 0.3 to about 1.0 percent.

Non-limiting examples of salts which are useful in practicing the invention are chlorides such as sodium chloride, potassium chloride, lithium chloride, calcium chloride, magnesium chloride and the like; or sulfates such as sodium sulfate, potassium can be released when contacted by a solution at the predetermined pH.

Using the conditions described herein, the polymers form hollow or solid matrix type microspheres wherein the cargo/fragrance is distributed in a carrier matrix or capsule type microspheres encapsulating liquid, vapor, or solid cargo. The amount of fragrance which may be incorporated by the microsphere is dependent on a number of factors which include the amount of material mixed with the monomer solution, as well as the affinity of the fragrance agent for the monomers. The polymer microspheres do not alter the properties of the fragrance. Any fragrance can be incorporated within the microspheres. The system is particularly advantageous for controlling the delivery of fragrance to a specific place and/or at a specific time. The targets can vary depending upon the fragrance employed.

The preferred microspheres have diameters between about 1 microns and about 500 microns, preferably between about 100 microns and about 250 microns. The microspheres can be readily blended with other solid or liquid ingredients which require a sustained release of a fragrance or a perfume agent, i.e., detergents, fabric softeners or lotions.

The size of the polymer microspheres formed by the method described herein can be controlled by manipulating a variety of physical or chemical parameters, such as the speed of the mixing during polymerization, monomer composition and the chemical structure of the fragrance.

The monomers, reagents and other additives used in practicing the present invention are commercially available from suppliers such as Aldrich Chemical Co. (Milwaukee, Wis., USA); Sigma Chemical Co. (St. Louis, Mo., USA); and Fluka Chemical Corp. (Ronkonkoma, N.Y., USA).

EXAMPLES

The following examples illustrate the invention without limitations. All monomers are used as received from the supplier, and may contain a small amount of inhibitor. The perfumes used, "MixTex 1" and Autre Melange" are available from Givaudan-Roure and contain several components. Cineole, also called "Eucalyptus Oil", and limonene are aroma materials used for trial encapsulations. The PVA employed in these examples had a M.W. of about 31–50,000 and was 87–89% hydrolyzed.

Example 1

In a flask equipped with a mechanical stirrer, a thermometer, a reflux condenser and inert gas inlet, 0.6 g of polyvinyl alcohol (PVA) was dissolved in 120 ml of distilled water at about 75–80° C. A solution consisting of 14.1 g of butyl methacrylate, 16.1 g of methacrylic acid, 0.9 g of benzoyl peroxide, and 2.3 g of the fragrance Autre Melange was then added to the PVA solution with continuous stirring, at 300 RPM, to produce an emulsion. The formation of solid particles began about 30–40 minutes after the organic monomer solution was added. The reaction temperature was raised from 80° C. to about 90–95° C. at the end of the polymerization process. Polymerization was complete after about 4–5 hours and the suspension was allowed to cool to ambient temperature. The solid product was filtered, washed with water, and dried at ambient temperature. The yield was quantitative.

Under an optical microscope the reaction product was shown to consist of smooth beads having diameters of 100–200μ. The dry beads had no detectable odor. However, they release a strong aroma on being dissolved in water at pH>8.0. The content of methacrylic acid in the co-polymer (based on potentiometric titration data) was 48%.

Example 2

Following the procedure of Example 1, co-polymerization of methacrylic acid and styrene in the presence of the fragrance Autre Melange was effected. A mixture comprising g of methacrylic acid, g of styrene, 3.2 g of benzoyl peroxide, and 11 g of fragrance was emulsified in 480 ml of 0.5% PVA in water, and polymerized at 80–90° C. for 5 hours. Polymer beads having diameters of 70–120μ, 114 g, were obtained. A methacrylic acid content of 46% in the co-polymer was found. The odorless beads release a strong scent of perfume when dissolved in water at a pH>8.0.

Example 3

Following the procedure of Example 1, a mixture of 14.5 g of methacrylic acid, 12.8 g of ethyl methacrylate, 0.7 g of AIBN, and 2.1 g of Autre Melange fragrance was emulsified with 120 ml of 0.5% PVA in water and polymerized at 65–75° C. for 4.5 hours, 29.7 g of the polymer beads having diameters of 40–100μ were obtained. The odorless beads dissolved at pH>8.0 and released a strong scent of perfume.

Example 4

Following the procedure of Example 1, a mixture of 9.2 g of methacrylic acid, 19.8 g of methyl methacrylate, 0.8 g of benzoyl peroxide, and 1.4 g of the fragrance Autre Melange was emulsified in 120 ml of 0.5% PVA in water and polymerized at 70–85 ° C. for 3 hours. 26 g of beads were obtained. The encapsulated fragrance was released more slowly due to the lower solubility in basic water of the co-polymer which contained only 31% of methacrylic acid.

Examples 5–21

Following the procedure of Example 1, polymers with encapsulated Autre Melange fragrance were obtained. The monomers, stabilizer and encapsulation results are tabulated in Table I These examples produced odorless beads which were soluble at pH>8.0 and released a strong scent of perfume.

TABLE 1

| Example No. | Monomers[1] | Stabilizer[2] Type/% | Wt. % Fragrance Added/Found[3] | Yield (wt %) | % RCOOH Added/Found[3] | % COOH Found[3] | Particle size [μ]/shape | Shape |
|---|---|---|---|---|---|---|---|---|
| 5 | MAA:MMA | PVA/.5 | 5.0/3.3 | 93 | 52/52 | 27.3 | 100–200 | round |
| 6 | MAA:MMA | PVA/.5 | 7.0/ | 87 | 46.5/43 | 22.4 | 50–120 | smooth round |
| 7 | MAA:Sty | PVA/.5 | 6.5/ | 90.2 | 45.4/43.8 | 22.9 | 100–150 | various |
| 8 | MAA:Sty | PVA/.5 | 6.7/ | 74.5 | 45.2/44.0 | 23.0 | 40–110 | various |
| 9 | MAA:BuMA | PVA/.5 | 6.9/ | 82.7 | 48.2/48.2 | 25.2 | 100–200 | smooth round |
| 10 | MAA:BuMA | PVA/.5 | 7.5/ | 90.1 | 57.7/57.2 | 29.9 | ~100 | various |
| 11[4] | MAA:BuMA | PAA/.5 | 6.9/ | 88.0 | 47.9/41.5 | 21.7 | .3–5 mm | irregular |
| 12 | MAA:BuMA | PVA/.5 | 7.0/ | 93.5 | 48.0/46.9 | 24.5 | 70–120 | smooth round |
| 13[7] | MAA:BuMA | PVA/.5 | 7.0/ | 97.3 | 41.8/45.7 | 23.9 | 100–180 | smooth round |
| 14 | MAA:EMA | PVA/.5 | 8.0/ | 94.7 | 47.4/48.6 | 25.4 | 90–120 | round uniform |
| 15 | MAA:EMA | PVA/.5 | — | 99.4 | 51.4/50.9 | 26.6 | 50–100 | round jagged |
| 16[5] | MAA:EMA | PVA/.5 | 7.0/ | 87.8 | 47.4/47.6 | 24.9 | 100–150 | round tendency to aggregate |
| 17[5] | MAA:EMA | PVA/.5 | 7.0/ | 98.9 | 48.2/49.2 | 25.7 | 40–100 | round tendency to aggregate |
| 18[6] | MMA:BuMA | PVA/.5 | 7.0/ | 83 | 48/45.3 | 23.7 | | Aggregates |
| 19 | MAA:BuMA | PVA/.5 | 9.1/ | 98.1 | 47.1/48.1 | 25.14 | 70–120 | round |
| 20 | MAA:BuMA | PVA/.5 | 9.0/ | 99.5 | 47.2/47.6 | 24.91 | 70–120 | round |
| 21 | MAA:Sty | PVA/.5 | 9.0/ | 94.6 | 50.0/46.1 | 24.1 | 70–120 | various |

Legend
[1]Monomers - MMA = methyl methacrylate, MAA = methacrylic acid, Sty = styrene, BuMA = butyl methacrylate, EMA = Ethyl Methacrylate
[2]Stabilizers - PVA = polyvinyl alcohol; PAA = polyacrylic acid
[3]Found after analysis of polymer
[4]Water solution contained 7.5% of sodium sulfate
[5]AIBN initiator
[6]Sonicated before polymerization, stirring speed 600 RPM.
[7]Aqueous/organic phase ratio 5:1, 7.5% of salt 340 RPM.

Example 22

Following the procedure of Example 1, a mixture of 13.5 g of methacrylic acid, 12.2 g of butyl methacrylate, 0.8 g of benzoyl peroxide, and 3.0 g of cineole was emulsified with 120 ml of 0.5% PVA in water and polymerized at 80–90° C. for 4 hours. Smooth beads, 28.7 g, having diameters of 100–120μ were recovered. The copolymer contained 46% of methacrylic acid and released a strong specific smell of eucalyptus oil when dissolved in basic water at pH>8.0. The copolymer encapsulated 70% of the cineole from the reaction mixture, based on gas chromatography analysis.

Examples 23–26

Following the procedure of Example 22, polymers with encapsulated Limonene or Cineole fragrance were prepared. The monomers, amount of fragrances and encapsulation results are tabulated in Table 2. These examples produced odorless beads which were soluble at pH>8.0 releasing a strong scent of fragrance.

TABLE 2

| Example No. | Monomers[1] | Stabilizer[2] Type/% | Wt. % Fragrance | Fragrance | Yield (wt %) | % COOH Found[3] | Particle size [μ]/shape | Shape |
|---|---|---|---|---|---|---|---|---|
| 23 | MAA:BuMA | PVA/.5 | 10.0 | Limonene | 97.3 | 23.7 | 100–130 | round |
| 24 | MAA:BuMA | PVA/.5 | 10.2 | Cineole | 96.8 | 24.0 | 100–120 | round |
| 25 | MAA:BuMA | PVA/.5 | 24.9 | Cineole | 89.4 | 21.1 | 100–180 | round |
| 26 | MAA:BuMA | PVA/.5 | 34.7 | Cineole | 80.1 | 18.8 | 75–100 | round |

Legend for Table 2
[1]Monomers - MAA = methacrylic acid, BuMA = butyl methacrylate
[2]Stabilizer - PVA = polyvinyl alcohol.
[3]Found after analysis of polymer.

Examples 27–29

Following the procedure of Example 1, polymers containing MixTex 1 fragrance were prepared. The monomers, amounts of fragrance and encapsulation results are tabulated in Table 3. These examples produced odorless beads which were soluble at pH>8.0 releasing a strong scent of fragrance.

TABLE 3

| Example No. | Monomers[1] | Stabilizer[2] Type/% | Wt. % Fragrance | Yield (wt %) | % RCOOH Added/Found[3] | % COOH Found[3] | Particle size [μ]/shape | Shape |
|---|---|---|---|---|---|---|---|---|
| 27[4] | MAA:EMA | PVA/.5 | 7.0 | 90.7 | 48.3/48.2 | 25.2 | 100–200 | round tendency to aggregate |
| 28 | MAA:EMA | PVA/.5 | 7.0 | 66.6 | 47.7/45.1 | 23.6 | 80–130 | round tendency to aggregate |
| 29 | MAA:EMA | PVA/.5 | 7.0 | 75.5 | 47.3/48.4 | 25.3 | 40–70 | round tendency to aggregate |

Legend
[1]Monomers - MMA = methyl methacrylate, EMA = Ethyl Methacrylate
[2]Stabilizers - PVA = polyvinyl alcohol; PAA = polyacrylic acid
[3]Found after analysis of polymer
[4]Water solution contained 5% of sodium sulfate All patents, applications, publications, and test methods cited herein are hereby incorporated by reference.

What is claimed is:

1. A method of releasing a fragrance comprising:
   a. encapsulating a fragrance within a copolymer consisting of from about 20% to about 80% by weight of an acrylic acid monomer and at least one ethylenically unsaturated polymerizable monomer;
   b. exposing the polymer encapsulated fragrance to a solution having a pH which dissolves the polymer and releases the fragrance.

2. The method of claim 1, wherein the acrylic acid monomer has the following formula

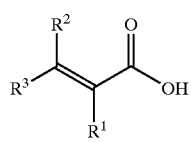

wherein $R^1$, $R^2$ and $R^3$ are independently selected from the group consisting of hydrogen and lower alkyl.

3. The method of claim 2, wherein the lower alkyl is a $C_1$–$C_6$ alkyl.

4. The method of claim 2, wherein the acrylic acid monomer is methacrylic acid.

5. The method of claim 1, wherein the ethylenically unsaturated polymerizable monomer is selected from the group consisting of acrylates, methacrylates, vinyl pyridines, vinyl ethers, acrylamides, methacrylamides, pyrrolidones, and styrenes.

6. The method of claim 1, wherein the ethylenically unsaturated polymerizable monomer is selected from the group consisting of butyl methacrylate, styrene, ethyl methylacrylate, and methyl methylacrylate.

7. The method of claim wherein the fragrance comprises a liquid, a solid, a vapor or a combination of any of the foregoing.

8. The method of claim 1, wherein said fragrance comprises a mixture of two or more essential oils.

9. The method of claim 1, wherein the solution has a pH greater than 7.0.

10. The method of claim 1, wherein the solution has a pH greater than 8.0.

11. The method of claim 1, wherein the solution has a pH less than 7.0.

12. The method of claim 1, wherein said polymer encapsulated fragrance is adapted to release said fragrance in a timed and sustained manner.

* * * * *